United States Patent [19]

Yianni et al.

[11] Patent Number: 5,496,581
[45] Date of Patent: Mar. 5, 1996

[54] POLYMERIC COATING

[75] Inventors: Yiannakis P. Yianni; Martin C. Wiles, both of Middlesex, United Kingdom

[73] Assignee: Biocompatibles Limited, Middlesex, England

[21] Appl. No.: 146,110

[22] PCT Filed: Jun. 5, 1992

[86] PCT No.: PCT/GB92/01012

§ 371 Date: Nov. 10, 1993

§ 102(e) Date: Nov. 10, 1993

[87] PCT Pub. No.: WO92/21386

PCT Pub. Date: Dec. 10, 1992

[30] Foreign Application Priority Data

Jun. 7, 1991 [GB] United Kingdom ............ 9112267

[51] Int. Cl.$^6$ .................. B05D 3/04; B05D 1/02; B05D 1/18; A61K 41/00
[52] U.S. Cl. .......... 427/2.12; 427/2.3; 427/301; 427/535; 427/240; 427/421; 427/430.1
[58] Field of Search ............... 427/2.31, 2.12, 427/2.24, 2.25, 2.3, 301, 535, 536, 421, 240, 430.1

[56] References Cited

U.S. PATENT DOCUMENTS

| | | | |
|---|---|---|---|
| 4,421,791 | 12/1983 | Kekish et al. | 427/239 |
| 4,560,599 | 12/1985 | Regen | 427/407.1 |
| 4,689,386 | 8/1987 | Chapman et al. | 427/385.5 |
| 4,931,498 | 6/1990 | Pidgeon | 525/54.1 |
| 4,933,114 | 6/1990 | O'Brien et al. | 260/403 |
| 4,963,367 | 10/1990 | Ecanow | 424/485 |
| 4,990,357 | 2/1991 | Karakelle et al. | 427/2.12 |
| 5,023,108 | 6/1991 | Bagaria et al. | 427/2.15 |
| 5,053,048 | 10/1991 | Pinchuk | 427/2.31 |
| 5,063,090 | 11/1991 | Wannlund | 427/2.11 |
| 5,135,297 | 8/1992 | Valint, Jr. | 427/430.1 |
| 5,217,743 | 6/1993 | Farah | 427/400 |
| 5,288,517 | 2/1994 | Kanno et al. | 427/299 |
| 5,380,904 | 1/1995 | Chapman et al. | 427/2.3 |

FOREIGN PATENT DOCUMENTS

| | | |
|---|---|---|
| 0032622 | 7/1981 | European Pat. Off. . |
| WO91/00745 | 1/1991 | WIPO . |

OTHER PUBLICATIONS

Derwent Abstract 105:12069 of WO8504326A1, Oct. 1985, Chapman et al.
Thin Solid Films, 132 (1985) pp. 1–10 and 11–19. (no month available).
Chemical Abstracts, 87 (1977) 152582a. (no month available).

*Primary Examiner*—Diana Dudash
*Attorney, Agent, or Firm*—Sughrue, Mion, Zinn, Macpeak & Seas

[57] ABSTRACT

A process for coating a surface comprising applying a solution containing a polymer obtained by polymerizing a phospholipid of the following formula (I):

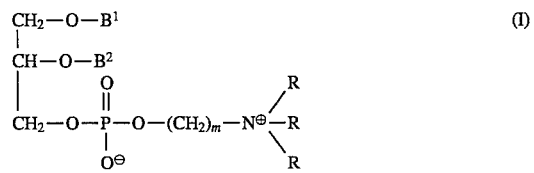

(I)

24 Claims, No Drawings

POLYMERIC COATING

The present invention relates to the treatment of the surfaces of materials to prevent or inhibit adsorption of protein or reduce thrombogenicity.

In blood contacting devices problems can arise from thrombogenic reaction at untreated metal, glass or plastic surfaces. Such a reaction can lead to platelet adhesion and clotting, which can have severe, sometimes disastrous, consequences. It is desirable therefore to develop a treatment for surfaces which reduces and preferably avoids such a reaction.

Problems can also arise from non-specific protein adsorption at the surface of devices used in many applications, such as medical devices. For instance, in many modern diagnostic devices, such as many biosensors, a specific interaction between an analyte and a detector species is relied upon. In such situations non-specific protein adsorption can cause a dramatic loss in sensitivity or even render the device inoperable. Similarly, where bioseparation membranes are used, non-specific protein adsorption can cause clogging and thus fouling of the membranes.

Protein adsorption is also recognised as a problem in sight correction devices such as contact lenses. Protein build up on such devices leads to a loss in comfort to the wearer and a deterioration in vision.

Many modern surgical and other medical procedures involve the use of blood-contacting devices, such as surgical implants, prostheses, catheters, drains and extra-corporeal circuitry. Such devices are used and then discarded for hygiene reasons: such devices must therefore be constructed from the most economical materials available, usually polymeric plastics or glass. However as already mentioned glass and most synthetic and natural polymers tend to induce platelet adhesion and activation. Initiation of the clotting cascade follows, leading to blockage of tubing and clogging of other apparatus such as filtration and dialysis membranes and interference with test procedures which, in certain cases, may have disastrous consequences for patients. Moreover in cases where a device is intended to be implanted into a patient and to remain for a prolonged period, such platelet aggregation and clotting must be avoided over a prolonged period.

With existing technology, in order to prevent the formation of blood clots during extra-corporeal circulation for haemodialysis, long term gas exchange at states of severe respiratory failure and cardiac support, e.g. after cardiac surgery, systemic heparinisation is employed. Owing to the risk of excessive bleeding after such systemic anticoagulant treatment many patients are disqualified from possible therapeutic measures. Likewise, commercial catheter sensors, e.g. for continuous determination of arterial oxygen, carbon dioxide concentration and of pH in the critically ill patient require systemic heparinisation to prevent microclotting on the sensor membranes and failure of the device.

It has been suggested that heparinisation of apparatus, particularly involving end point attachment of heparin fragments, will result in anti-thrombogenic coating of surfaces and thereby overcome the need for systemic heparinisation. Thus a method was developed in which heparin was coupled by end point attachment [Hoffman, J. et al., *Carboyhdr. Res.*, 117:328(1983), Larm, O. et. al., *Biomat. Med. Dev. Art. Org.*, 111161(1983)]. The resulting surfaces adsorbed antithrombin and large amounts of thrombin which were rapidly inhibited in the presence of antithrombin [Pasche, B, et al., *Thromb. Res.*, 44 739(1986)]. It is interesting to note that end-point attached heparin and the endothelium behave both quantitatively and qualitatively alike with respect to the inhibition of thrombin in the presence of plasma [Arnander C., et al., *J. Biomed. Mat. Res.*, 20:235(1986)] and that a polyethylene surface furnished with end-point attached heparin showed considerable capacity to inhibit Factor Xa [Kodama, K. et al., *Thromb. Haemostas.* (1987)].

Rigid polyethylene tubing sections with end-point attached heparin have been kept in the thoracic aorta of pigs for up to four months [Arnander C., et al., *Biomat. Res.*, (1987)]. When applied to vascular grafts of expanded polytetrafluoroethylene (PTFE) and to polyurethanes and implanted in the arteries of the sheep [Esquivel, C. O. et al., *Surgery*, 95:102(1984)], the end-point attached heparin surface substantially reduced the platelet and fibrin deposition. The extra-corporeal circulation of blood through surface-heparinised devices offered the possibility to discriminate between the role of platelets and the plasma coagulation system as the main determining factor for achieving thromboresistance. In these experiments, it was demonstrated that coatings with other sulphated polymers were as platelet compatible as the heparin coatings, but still thrombogenic. Using the radioimmunoassay for fibrinopeptide A [Nossel, H. L. et al., *J. Clin. Invest.*, 54:43 (1974)] it was shown that only coatings on which the heparin molecules could interact with plasma constituents were able to prevent conversion of fibrinogen to fibrin on contact with blood [Larsson R. and Lindahl U. *Artif. Org.*, Vol 3. Suppl. Proc. of the second meeting of the Intern. Soc. Artif. Org., (1979); Larsson R., et al., *Thromb. Res.*, 19:43(1980); Larm, O. et al., *Biomat. Med. Dev. Art. org.*, 11:161(1983)].

Thus the presence of intact functional groups on the immobilised heparin appeared mandatory for achieving thromboresistance and heparin coatings on blood-contacting medical devices could eliminate hazardous systemic anticoagulant treatment.

Experimental haemodialysis has been performed on dogs without systemic heparinisation and with cellulose acetate hollow fibre filters with end-point attached heparin surfaces. The efficiency of the coating on the total extra-corporeal system was demonstrated by the fact that the levels of fibrinopeptide A in the dialysed animals were not higher than in anaestahetised control animals with no surgery [Arnander C., et al., *Proc. Eur. Soc. Art. Org.*, 9:312(1982), Lins, L.-E et al., *Proc. EDTA-ERA*, 21:270(1984)]. When end-point attached heparin surfaces were used in the extra-corporeal circuit, reno-venous by-pass for carbon dioxide elimination was easily performed for 24 h on dogs in a steady-state condition. After a small release of heparin, the coagulation system seemed unaffected as determined by fibrinopeptide A levels in the circulating blood [Larm, O. et al., An approach to antithrombosis by surface modification. Progress in artificial organs, ISAIO Press, Cleveland 1986, p313. Inacio, J. et al., Extracorporeal elimination of carbon dioxide using a surface heparinised vein-to-vein bypass system. EUROXY Workshop on design and techniques of extra-corporeal gas exchange. Paris, Jun. 20, 1985. Bindsley L., et al., *Trans. Am. Soc. Art. Int. Org.* 32:530(1986)]. Although heparinisation can reduce or prevent clotting, this is at the expense of interference with the blood biochemistry, for instance the complexation of antithrombin and other subtle alterations. The heparinised surfaces are exerting many of the effects of heparin when administered as an anti-coagulant drug and the adverse side effects of heparin must, therefore, be taken into account when this technique is employed to improve haemocompatibility of blood-contacting devices.

Much effort has been devoted in recent years to the development of surface treatments, especially by covalent bonding of haemocompatible organic groups which improve the biocompatibility of blood-contacting surfaces and to the production of more biocompatible materials for use in blood-contacting devices such as surgical implants, prostheses and artificial hearts (see, for instance EP-A-0032 622 and EP-A-0 157 496).

In particular EP-A-0032622 discloses di-acetylenic phospholipids which may be used to coat blood contacting surfaces. The coated surface may subsequently be irradiated with actinic radiation, (e.g. ultra violet radiation) to provide a polymerised stable coated surface and improve the biocompatibility of blood-contacting surfaces. Such a procedure is however, not suitable for application to blood-contacting surfaces which cannot be readily exposed to radiation, such as ultra-violet radiation, for instance by virtue of their position (such as the interior surfaces of tubes), or because they are sensitive to gamma irradiation, for example polyvinylchloride (PVC) surfaces.

We have now devised a simple process for reducing the thrombogenicity of blood-contacting surfaces or inhibiting or preventing the non-specific adsorption of protein surfaces which may be used successfully with surfaces, which are inaccessible to ultra-violet radiation and/or sensitive to gamma-irradiation. The surface is coated with a stable coating so that thrombogenicity or protein adsorption will be avoided over a prolonged period.

We believe that the coatings used in the present invention may be regarded as non-thrombogenic and involving no interference with blood biochemistry rather than as anti-thrombogenic.

Such coated surfaces therefore have applications in blood contacting devices and in devices where reduced non-specific protein adsorption is desirable, for instance in diagnostic devices which require a specific interaction of an analyte and detector species, e.g. biosensors, bioseparation membranes and sight correction devices.

Treated surfaces showing such advantageous properties may be described as having improved biocompatability compared to untreated surfaces.

It has also been found that surfaces coated by the process of the present invention possess no net surface charge. Such properties lead the process of the invention to have further applications for instance in the electronics industry and in electrochemical detection and analysis where electrostatic charge or interfering background charge needs to be minimised.

In addition the present invention offers the further advantages in many applications that the coated surfaces have improved wettability and improved lubricity. This assists in, for instance, avoiding the formation of gas bubbles in tubing and facilitating insertion of catheters via surgical incisions.

According to the invention there is provided a process for coating a surface comprising applying to the surface a solution or suspension of a polymer, in an organic solvent, and removing the solvent, wherein the polymer is obtainable by polymerising a phospholipid of formula (I):

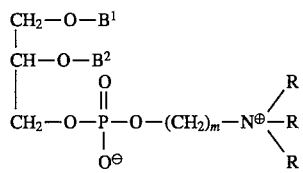

wherein at least one of $B^1$ and $B^2$ is a group of the formula (II):

$$-(CO)_p-X^1-C\equiv C-C\equiv C-Y^1 \quad (II)$$

wherein p is 0 or 1, preferably 1, $X^1$ is an aliphatic or cycloaliphatic group, $Y^1$ is H or a monovalent aliphatic or cycloaliphatic group, the total number of carbon atoms in $X^1$ and $Y^1$ in each $B^1$ and/or $B^2$ being 8 to 26, and the other of $B^1$ and $B^2$ is either (a) the same or a different group of the formula (II) or (b) is an aliphatic or cycloaliphatic group containing at least 8 carbon atoms; m is 2, 3 or 4 and each R independently represents an alkyl group containing 1 to 4 carbon atoms.

The polymers used in the process of the invention will normally contain repeat units of the formula (III):

where two of $Z^1$, $Z^2$, $Z^3$ and $Z^4$ are each groups of formula $Y^1$, as defined above the other two of $Z^1$, $Z^2$, $Z^3$ and $Z^4$ are each of formula $-X^1-(CO)p-G$ where $X^1$ and p are as defined above and G is the corresponding remaining portion of the phospholipid of formula (I). In particular they may contain repeat units linked between opposite ends of the diacetylenic unit, where $Z^1$ and $Z^4$ or $Z^2$ and $Z^3$ are of formula $Y^1$ and $Z^2$ and $Z^3$ or $Z^1$ and $Z^4$ are of formula $-X^1-(CO)_p-G$, i.e, groups of formula (IV):

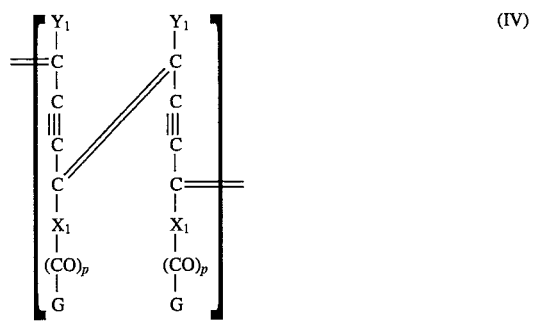

The conjugated di-ynes of formula (I) have a zwitterionic group of formula (V):

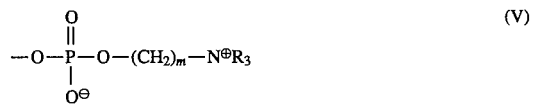

The preferred zwitterionic group is the analogue of the phosphate-linked group of the natural phospholipid lecithin and sphingomyelin, namely the choline phosphate group wherein m is 2 and R is methyl. While it is preferred that each R group is methyl, as it is in naturally occurring products the groups, R may alternatively be ethyl, propyl or butyl and may be the same or different.

In one embodiment of the invention in the conjugated diynes of formula (I), both $B^1$ and $B^2$ are groups of the formula (II) which are the same or different. Symmetrical compounds that is to say compounds in which $B^1$ and $B^2$ are the same, are the easiest to synthesise and are therefore preferred.

The position of the conjugated di-yne system in the $B^1$ and $B^2$ residue is not critical. It is for example possible for the conjugated di-yne system to be at the end of the hydrophobic chain remote from the carboxylic ester or ether function so that $Y^1$ is hydrogen and $X^1$ contains at least 8 carbon atoms. However, it is usually more convenient to arrange for the conjugated di-yne system to be located towards the centre of the hydrophobic chain so that there is approximately the same number of carbon atoms in $X^1$ and $Y^1$.

$X^1$ and $Y^1$ are each preferably an aliphatic or cycloaliphatic group and more preferably each unbranched saturated hydrocarbon compounds. However $X^1$ and $Y^1$ may alternatively be aliphatic or cycloaliphatic groups containing branched-chain hydrocarbon moieties or containing substituents on the hydrocarbon chains, for example alkoxy substituents or halogen. It is also possible for the groups $X^1$ and $Y^1$ to contain carbon-carbon unsaturated bonds. The total number of carbon atoms in $X^1$ and $Y^1$ in each group $B^1$ and $B^2$ of formula (II) is from 8 to 26 carbon atoms so that each hydrophobic chain contains a total of 12 to 30 carbon atoms excluding any carbonyl carbon atoms. We have found that if the group $B^1$ and/or $B^2$ contains less than 12 carbon atoms, the resulting material is difficult to polymerise except at very low temperatures. As a practical matter, we find that the most satisfactory results are obtained when there is from 16 to 26 carbon atoms, particularly 20 to 26 carbon atoms, in the groups $B^1$ and/or $B^2$ excluding any carbonyl carbon atoms.

Preferred compounds of formula (I) include those in which $B^1$ and $B^2$ are both groups of formula (II), $X^1$ is the group —$(CH_2)_8$— and preferably p is 1.

The groups $X^1$ and $Y^1$ can also include cycloaliphatic residues containing 3 to 8 or even more carbon atoms in a cycloaliphatic configuration.

For reasons which will become apparent from the discussions below concerning polymerisation of the conjugated di-ynes, it is preferred that both $B^1$ and $B^2$ include the conjugated di-yne system so that the conjugated di-yne system can participate in both intramolecular and intermolecular polymerisation. However, a sufficient degree of polymerisation can be obtained simply by intermolecular polymerisation in which case it is only essential that one of the groups $B^1$ and $B^2$ contain the conjugated di-yne system. Indeed in some cases it is preferred to use a di-yne in which only one of $B^1$ and $B^2$ contains a conjugated di-yne system, so that a linear phospholipid polymer is obtained and not one which contains cross-linking between polymer chains.

When only one of $B^1$ and $B^2$ contains the conjugated di-yne system, the other of $B^1$ and $B^2$ may be an aliphatic or cycloaliphatic residue, preferably hydrocarbon residue, which can be saturated or may contain olefinic or perhaps single acetylchic unsaturation which can be isolated or in conjugation with the conjugated di-yne system. Such groups are again bonded to the glycerol residue through an ester or ether group and should again contain at least 12 carbon atoms.

The most preferred phospholipids of formula (I) are 1,2 ditricosanoyl-10,12-diyne-sn-glycero-3-phosphorylcholine and 1,2-dipentacosanoyl-10,12-diyne-sn-glycero-3 -phosphorylcholine, i.e. compounds of formula:

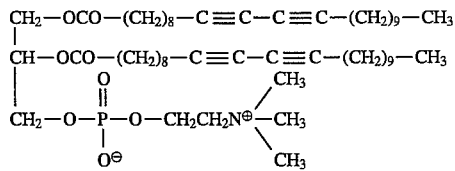

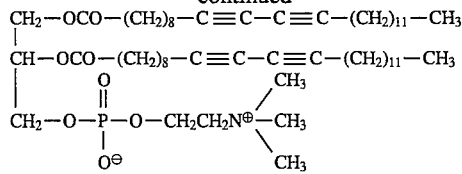

The conjugated di-ynes of formula (I) may be prepared by procedures described in EP-A-0032622.

The conjugated di-ynes of formula (I) can be polymerised by subjecting them to actinic radiation, normally gamma radiation. Such irradiation produces a polymerisation between the conjugated di-yne systems in adjacent diacetylenic chains. This gives rise to a polymer containing repeat units of the formula (III) as hereinbefore defined.

When both $B^1$ and $B^2$ contain conjugated di-yne systems, there will be both intramolecular and intermolecular reaction which is desirable to provide a coating which will be as stable as possible. For this reason, it is preferred that both $B^1$ and $B^2$ contain the conjugated di-yne system and, in order to optimise the intramolecular reaction, it is preferred that the relative positions of the conjugated di-yne system in $B^1$ and $B^2$ be approximately the same, in other words, that the carbon chains connecting the conjugated di-yne systems to the glycerol residue should not differ in length by more than 2 carbon atoms.

However in those cases when a di-yne containing a conjugated di-yne system in both $B^1$ and $B^2$ is used, some solvent insoluble polymer may be obtained due to crosslinking between polymer chains. This may be controlled by selecting the reagents and reaction conditions to minimise such cross-linking and/or by separating the soluble (hence linear) polymer from the insoluble cross-linked material.

Pre-polymerisation is normally induced by exposure to gamma radiation, but in principle, any method known to be capable of inducing polymerisation of conjugated di-yne systems can be used for the production of the polymers used in this invention.

The phospholipid may be pre-polymerised in any form in which there is significant alignment of the molecules (for instance in the solid phase or in the presence of water).

Typically the phospholipid of formula (I) is polymerised in solid bulk form, by exposure to gamma radiation of wavelength from 0.05 to 14 nm and at doses of from 1 to 50, preferably 2 to 10, e.g. 2.5 M. Rads: the exact dosage will depend upon the extent of polymerisation which is required. This procedure may be performed on dry, fine powdered, phospholipid.

Alternatively the phospholipid of formula (I) can be pre-polymerised using ultra-violet radiation. Generally short wavelength UV radiation, e.g. having a wavelength of about 254 nm is used. Typically the irradiation is performed on dry powdered phospholipid but in this case it is necessary to stir the phospholipid regularly to ensure that the bulk of the material is exposed to the radiation.

The phospholipid of formula (I) can also be pre-polymerised as a thin layer on a substrate, removed from the substrate and used in the process of the present invention. Suitable substrates include glass or polyethylene. The thin layer may be formed by dissolving the phospholipid in a solvent such as chloroform or ethanol, and slowly evaporating the solvent on the substrate. The use of such a thin-layer helps to orient the phospholipid molecules during polymerisation. After irradiation the resulting polymer may be removed from the substrate e.g. by scraping or by dissolving in an organic solvent.

The phospholipid of formula (I) can also be pre-polymerised in the form of an aqueous solution or suspension.

The conjugated di-yne may be irradiated in the form of liposomes in an aqueous phase, which may be prepared by known methods. Such liposomes can for example be prepared by dispersion of the conjugated di-yne in an aqueous medium, raising the temperature of the dispersion to one above the lipid or Chapman transition temperature which is the temperature at which liposome formation occurs and then cooling the dispersion back to ambient temperature. However when polymerisation is performed on liposomes cross-linking between polymer chains often occurs producing an insoluble polymer. In this case it is therefore preferred to use a phospholipid in which only one of the groups $B^1$ and $B^2$ contains a conjugated di-yne system.

As yet a further alternative the conjugated di-yne can be pre-polymerised by irradiation in the form of an emulsion between an aqueous and an organic phase. Suitable organic phases for such an emulsion may comprise chloroform, dichloromethane, or diethyl ether.

The pre-polymerised phospholipid may be separated from unpolymerised phospholipid of formula (I) and any material cross-linked between polymer chains prior to coating on the surface. This can be achieved by exploiting the different solubility of the -unpolymerised monomer, pre-polymerised polymer and cross-linked material in organic solvents. For example the solubility of monomeric and pre-polymerised material and insolubility of cross-linked material in chloroform may be used to remove cross-linked material. Pre-polymerised material may then be separated from monomeric material using acetonitrile (e.g. at 50° C.) in which monomer is soluble and polymer insoluble. Alternatively, separation of monomeric and pre-polymerised material may be obtained on a gel permeation chromatography column, using for example a chloroform/ethanol mixture (e.g. 1:1), as a solvent.

Alternatively the phospholipid may be coated onto the surface as a mixture of polymer and monomer species without further purification, which does have considerable advantages in terms of cost effectiveness.

Prior to coating the surface the polymerised phospholipid may be mixed with one or more fatty acid diesters of phosphatidyl choline.

The fatty acid diesters of phosphatidyl choline which may be used in the process of the invention include esters of saturated and unsaturated fatty acids and may be pure single compounds such as distearoyl phosphatidyl choline (DSPc), dipalmitoyl phosphatidyl choline (DPPC) and dimyristoyl phosphatidyl choline (DMPC), mixtures of such compounds and purified natural products such as the fatty acid diesters of phosphatidyl choline from egg yolk or soya bean lecithin. Mixed diesters of phosphatidyl choline may be used. Preferably the fatty acid side chains will be straight as opposed to branched and will have from 12 to 20 carbon atoms. Purified natural products may contain a small proportion of components other than fatty acid diesters of phosphatidyl choline but these should not generally be present in a sufficient amount to impair the biocompatibility of the coating. In particular, phosphatidyl serine, and other anionic phospholipids which would cause protein adsorption or blood clotting, should be avoided.

The use of these diesters of phosphatidyl choline may represent considerable economic advantages, since they are readily available. Where such a mixture is used in the process of the invention, it preferably comprises at least 10%, more preferably 20%, by weight of polymerised diacetylenic phospholipid to provide sufficient stability to the coating applied to the surface.

The surface to be treated may optionally be prepared for coating by washing to remove surface contaminants and, to improve the adhesion of the coating, by silylation, plasma polymerisation or otherwise to increase the hydrophobicity of the surface.

Pre-washing of the surface may be effected using a suitable solvent such as those described below which may be the same as or different to the solvent or solvent system used to apply the coating. The surface may also be cleaned by plasma etching in an oxygen atmosphere. Pre-treatment of the surface by silylation is preferably effected using a reactive alkyl silane such as a halo silane, for instance trichloro-octadecyl silane or chlorodimethyloctadecyl silane in a suitable solvent such as hexane or chloroform. Excess reagent may be removed by a further washing step.

As an alternative, pretreatment to increase hydrophobicity may be effected by a plasma polymerisation, under conditions giving a glow discharge e.g. by plasma barrel etching. Suitable monomers for use in such a pretreatment include alkanes containing from five to twenty preferably five to twelve carbon atoms, e.g. hexane, octane or decane and alkyl silanes containing from five to twenty, preferably twelve to twenty carbon atoms, e.g. octadecyl silanes or for example vinyl silanes.

The thickness of the coating will be selected according to the intended use of the device. Typical thicknesses envisaged for coatings according to the invention are in the order of 3 to 1000 nanometers, preferably 10 to 500 nanometers and most preferably about 100 nanometers.

The surface to be treated may be a blood-contacting surface, or it may be some other type of surface, e.g. the surface of a biosensor, bioseparation membrane, or the surface of an electronic device or component or of an electrochemical detection or analysis device. It may be a surface of a finished device such as a blood-contacting device or it may be the surface of a material to be used in forming a finished device. In the latter case subsequent forming steps are selected to avoid disrupting the coating formed by the process of the invention in portions of the device where the coating will protect the surface in use and to avoid chemical damage, for instance due to high temperatures, to the phospholipid coating. The surface being treated will hereinafter be referred to as the "substrate".

Examples of substrates which may be coated according to the invention include glasses (e.g. soda glass and silica glass), metals such as silver and stainless steel, natural polymers, such as cellulose and semisynthetic cellulose derivatives, and artificial polymers such as polyurethanes (e.g. Pellethans), vinyl polymers such as polyvinyl chloride (PVC), polyesters such as polyethylene terephthallate (e.g. Dacron), polyalkenes such as polyethylene and polypropylene, polycarbonates and polysulphones and fluoropolymers such as polytetrafluoroethylene (PTFE), polyvinylidene difluoride (PVDF) and other poly(fluoroalkenes) including fluorinated ethylene polymer (FEP) which is a copolymer of tetrafluoroethylene and hexafluoropropylene.

The solvent may be any conventional organic solvent which will dissolve or suspend the pre-polymerised phospholipid. Preferably the solvent will be selected for lack of toxicity and environmental hazards, for ease of removal, for compatibility with the material to be treated and for pharmacological acceptability. The solvent may be one which swells a polymeric substrate and this will aid the treatment process by permitting the pre-polymerised phospholipid to penetrate the surface of the substrate. Alternatively the solvent may be selected to avoid swelling of a polymer substrate, particularly where there are fine dimensional tolerances to be maintained or other useful properties of the polymer would be thereby impaired.

Preferred solvents include water, lower alkanols such as methanol, ethanol and iso- or n-propanol, halogenated alkanes such as dichloromethane, chloroform, alkanes containing typically from 5 to 10 carbon atoms, e.g. pentane or hexane, and mixtures thereof. A particularly preferred solvent is a mixture of ethanol and chloroform, such as from 20:1 to 80:1 preferably 40:1 ethanol:chloroform by volume. Another preferred solvent is a mixture of Freon and ethanol such as from 50:50 to 99:1, preferably 90:10 Freon:ethanol by volume.

The pre-polymerised phospholipid may be applied as a solution or as a suspension in an organic solvent. Where a suspension is used it will generally be sufficiently fine to ensure that a uniform coating of pre-polymerised phospholipid is obtained. Suspensions of pre-polymerised phospholipid may, for example be applied in water or mixtures of freon and ethanol as solvent.

The concentration of pre-polymerised phospholipid in the solvent will be selected to avoid use of unduly large quantities of solvent (and ensuing technical difficulties with removal thereof and economic penalties) whilst enabling efficient coating of the substrate. Preferred concentrations are in the range of from 0.5 to 35 mg/ml, preferably 2 to 20 mg/ml, e.g. 5 to 10 mg/ml.

The solution or suspension of pre-polymerised phospholipid may be applied by any conventional coating technique such as immersion in a coating bath, spraying, painting or, for flat substrates, spin-coating, the coating conditions being varied according to the desired thickness of coating and the hydrophobicity of the substrate since the phosphatidyl diesters adhere more strongly to more hydrophobic substrates. Preferably coating is achieved by immersion of the substrate in a bath of a pre-polymerised phospholipid solution or suspension in a suitable solvent at an appropriate concentration and temperature for sufficient time to cover the surfaces to be coated. The solvent may be removed by conventional techniques, preferably by evaporation under reduced or ambient pressure, in a gas stream and/or at elevated temperature. By careful selection of the solvent, concentration of the solution and coating and solvent removal techniques, the thickness of the phosphatidyl choline diester coating may be controlled within a desired range. Particularly preferred solvents, concentrations and coating and solvent removal techniques are described in detail and illustrated by the Examples.

Typical blood contacting devices whose blood contacting surfaces may be coated using the process of the present invention include tubing such as catheters, for instance central venous catheters, thoracic drain catheters, and angioplasty balloon catheters, tubing used in extra-corporeal circuitry such as in heart and/or lung bypasses and entire extra-corporeal circuits such as whole blood oxygenators, cannulae, vascular grafts, sutures, membranes such as those used in blood separation, apheresis and donorpheresis units, gas exchange membranes such as used in whole blood oxygenators, polycarbonate membranes and haemodialysis membranes and membranes used in diagnostic and biosensor devices, biosensors and other devices used in diagnosis such as cuvettes used in blood clotting time determinations, prostheses, artificial hearts and surgical implants.

Other devices may be treated to reduce non-specific adsorption of proteins including diagnostic devices such as biosensors, bioseparation membranes, sight correction devices such as contact lenses.

The following Examples serve to illustrate the invention and are not intended to limited it in any way.

REFERENCE EXAMPLES

Reference Example 1

Pre-polymerisation of DAPC

Dry, powdered 1 g of 1,2-dipentacosanoyl-10,12-diyne-sn-glycero- 3-phosphorylcholine, (DAPC) was subjected to 2.5 M.Rads of gamma-radiation (1 to 10 nm). The resulting material was 10% by weight soluble in ethanol/chloroform (40:1 v/v)and was a mixture of monomer and polymer (90:10) monomer by weight was determined following separation using gel permeation chromatography.

Gel Permeation Chromatography

The pre-polymerised DAPC may be separated from unpolymerised DAPC by gel permeation chromotography according to the following procedure:

A column (15 cm×3 cm diameter) is prepared using pre-swelled Sephadex LH60 (Pharmacia Fine Chemicals) in $CHCl_3$/Ethanol (50/50). The column is degassed before use. Chromatographic conditions are controlled using low pressure liquid chromatography hardware (Pharmacia) This consists of a PI peristaltic pump, a UVI detector with filter (280 nm) and a RECI recorder.

ppDAPC (500 mg) dissolved in the minimum volume of mobile phase ($CHCl_3$/Ethanol 50/50) is loaded onto the column. Separation is achieved using an isocratic system and a flow rate of 1.5 mls/minute. Fractions are collected every 12 minutes.

High molecular weight polymeric material elutes from the column with the solvent front. Lower molecular weight polymeric material elutes in order of decreasing molecular weight. Unpolymerised DAPC is eluted last.

UV visible spectroscopy and TLC may be used to identify the composition of fractions from the column. Polymeric fractions free from unpolymerised DAPC may be pooled. Unpolymerised DAPC fractions may be pooled for repolymerisation.

Solvent Extraction

Alternatively unpolymerised DAPC may be separation from polymeric DAPC using solvent extraction. Separation can be achieved using the fact that unpolymerised DAPC is soluble in acetonitrile up to a concentration of 50 mg/ml at 50° C., whereas polymerised DAPC is insoluble at 50° C., according to the following procedure:

ppDAPC (1 g) is treated with acetonitrile (50 ml) at elevated temperature (50° C.) for 5 minutes and the acetonitrile removed. The ppDAPC may be treated with acetontrile three more times in the same way and the washings combined and filtered. In this way at least 80% of unpolymerised DAPC is extracted. The remaining unpolymerised DAPC may be extracted by redissolving in chloroform, and repeating the procedure.

The remaining ppDAPC may be tested for unpolymerised DAPC by TLC, UV spectroscopy or by gel permeation chromotography.

TLC may be performed (silica plates) in $CHCl_3$/MeOH/ 25% $NH_3$ (690:270:45) and visualised with iodine and molbdenum blue.

Polymeric DAPC has an UV visible absorbance maxima at 450 nm. This peak is very broad and extends to the UV. Monomeric DAPC has a UV spectrum with 4 peaks at 210, 225, 240 and 250 nm purified ppDAPC is free of these UV peaks.

Reference Example 2

Reference Example 1 was repeated but using a dosage of 5.0 M.Rads. The resulting material was 88:12 monomer:polymer by weight.

Reference Example 3

Reference Example 1 was repeated but using a dosage of 7.5 MRads. The resulting material was 76:24 monomer:polymer by weight.

EXAMPLE 1

Treatment of PVC Tubing

Samples of hard and soft tubing of the type used in extra-corporeal circuitry were either washed with warm ethanol or filtered distilled water and thoroughly dried prior to coating.

Both types of tubing were coated in a dust free area to avoid contamination by pipetting a coating solution of pre-polymerised DAPC (ppDAPC) (produced according to the Reference Examples and separated from monomer) in ethanol:chloroform (40:1 v/v) or a very fine suspension in freon:ethanol (101 v/v), (5 mg/ml or 10 mg/ml) into the hollow tube and gently working the solution backwards and forwards (for sections up to 120 cm in length) until the whole of the inside of the tube was evenly coated.

Excess coating solution was then allowed to drain into a collection bath and the tubing allowed to dry at room temperature. Coatings produced by the above method were homogeneous as judged by surface analytical techniques.

EXAMPLE 2

Coating of polyethylene (PE) ribbon

PE ribbon was first washed in ethanol and dried. The ribbon was then dipped briefly into an ethanol:chloroform solution (40:1 v/v) of pre-polymerised DAPC (10 mg/ml concentration) and then air dried.

This was repeated using ppDAPC solutions containing a mixture of monomer and polymer produced by gamma-radiation at 2.5 MRads (monomer:polymer ratio of 90:10 by weight), 5.0 MRads (monomer:polymer ratio of 88:12 by weight) and 7.5 MRads (monomer:polymer ratio of 76:24 by weight).

The coatings obtained by the above method were homogeneous as judged by surface analytical techniques.

EXAMPLE 3

Coating of PE ribbon with mixed lipids

PE was coated with a solution (10 mg/ml) of a mixture of 75:25, 50:50 or 25:75 (w/v) ppDAPC/DPPC or ppDAPC/DMPC using the same procedure as Example 2.

EXAMPLE 4

Coating of polyethylene catheters

Catheters containing a titanium oxide additive were washed with Freon and coated by dipping in a ppDAPC (10 mg/ml) solution in Freon. The temperature was 25° C.

EXAMPLE 5

Coating of polyethylene terephthalate (PET) pharmaceutical vials

PET vials were first washed in ethanol and dried. An aliquot (1 ml) of a solution (2 mg/ml) of ethanol:chloroform (40:1) ppDAPC was pipetted into the vial and the vial slowly rotated until most of the solvent had evaporated. The vial was then inverted and excess solution was removed.

EXAMPLE 6

Coating of polyethylene terephthalate filtration membranes

Woven PET filter material of pore size 10 to 14 μm was cut to size and placed at the bottom of the coating vessel. A coating solution [0.5, 1.0, 2.5, 5.0, 7.5, 10 or 20 mg/ml ppDAPC in either chloroform, ethanol:chloroform (40:1 v/v), freon:ethanol (10:1 v/v) or freon] was poured over the filter. The coating solution was worked slowly over the complete surface of the filter by gently rocking the coating vessel. After 30 seconds the filter was removed from the vessel, the excess removed and then air dried by hanging in a laminar flow cabinet.

The porosity of the material was checked by Coulter porometery and found to be unaffected in all cases.

EXAMPLE 7

Coating of PE woven membranes with ppDAPC/DPPC mixtures

The procedure of Example 6 was repeated using mixtures of ppDAPC/DPPC (2.5 mg/ml ppDAPC and 7.5 mg/ml DPPC).

EXAMPLE 8

Coating of glass pharmaceutical vials

Glass vials were washed with ethanol and dried. An aliquot (1 ml) of a solution of ppDAPC (2 mg/ml) in ethanol:chloroform (40:1 v/v) was pipetted into a vial and the vial rotated slowly until most of the solvent had evaporated. It was then quickly inverted and the excess solution removed.

EXAMPLE 9

Coating of glass pharmaceutical vials

Glass vials were silylated, prior to treatment with ppDAPC to render the surface very hydrophobic, resulting in a layer of silane on which a very stable coating is formed. Silylation was carried out by the addition of a solution (0.1% w/v in chloroform) of monochlorodimethyloctadecylsilane to the vial. The vial was left for 16 hours to react and then emptied, washed with chloroform and air dried. The vials were then coated with ppDAPC using the procedure of Example 8.

EXAMPLE 10

Coating of polypropylene hollow fibre membranes

Polypropylene hollow fibres of the type used in oxygenators were first washed using Freon and dried prior to coating. ppDAPC solutions (2, 4, 5 and 10 mg/ml) were used to coat the material. In this case the ppDAPC was dissolved in freon:ethanol (9:1 v/v). The fibres were coated by slowly drawing them through a "U" shaped coating vessel filled with the ppDAPC solution and allowed to air dry.

The coating was shown to be only on the external surface of the hollow fibre using surface analysis techniques.

EXAMPLE 11

Coating of polypropylene pharmaceutical vials

Polypropylene vials were washed with ethanol, dried and coated using the procedure of Example 8.

EXAMPLE 12

Coating of polystyrene petri dishes by spin coating

Petri dishes (sterilin polystyrene microbiological plates produced aseptically) were spun (1500 rpm) and 1 ml of a solution of ppDAPC (10 mg/ml) in ethanol:chloroform (40:1) were applied to the spinning dishes using a 1 ml pipette. Samples were spun for 30 seconds and then allowed to dry at room temperature.

EXAMPLE 13

Coating of polyester yarn suture material

Samples of dyed and undyed braided polyester yarn suture material were washed in warm ethanol and air dried prior to coating. The washed and dried samples were coated by drawing the suture through a "U" tube containing a ppDAPC (10 mg/ml) solution in ethanol:chloroform (40:1) followed by air drying at room temperature.

EXAMPLE 14

Coating of silver film by spin coating

A silver film formed by vacuum deposition on glass was coated by spin coating at varying speeds between 550–2000 rpm. ppDAPC solutions (1.25, 2.5, 5.0 and 10 mg/ml) in ethanol:chloroform (40:1) were used. The coating was judged to be homogeneous as determined by surface analytical techniques.

EXAMPLE 15

Coating of silver film by spin coating

Silver films vacuum deposited on glass substrates were cleaned with ethanol and dried before coating. They were immersed in a solution (2 mM) of 1-decane thiol and left overnight to react. The resulting surface was very hydrophobic. The silver films were then coated according to Example 14 above.

EXAMPLE 16

Coating of polished stainless steel rods

Polished stainless steel rods were cleaned with ethanol and dried. The rods were then coated from an ethanol:chloroform (40:1) v/v ppDAPC solution (10 mg/ml) by dipping directly into the solution. The rods were left to air dry.

EXAMPLE 17

Coating of polyimide

Kapton (polyimide) was cleaned with ethanol and dried. The material was coated from an ethanol:chloroform (40:1 v/v) solution of ppDAPC (10 mg/ml) by dipping directly into the solution. The material was then air dried.

EXAMPLE 18

Treatment of IV catheters

IV catheters made of FEP (fluorinated ethylene polymer) were coated with ppDAPC using a dipping technique. ppDAPC (10 mg/ml) was dissolved in ethanol:chloroform (40:1 v/v) and samples immersed in this solution for a few seconds. The catheters were then air dried.

EXAMPLE 19

Plasma Etching and Octane Treatment

Samples of polyamide mesh, stainless steel needles, PTFE tubing and polypropylene were washed in hexane and dried. The samples were placed in the etching chamber of a plasma barrel etcher (RF Plasma Barrel Etcher PT7100 available from Bio-Rad, Polarion Division).

The samples were etched under an oxygen atmosphere (5 minutes). The samples were then placed under an Argon atmosphere in the presence of octane (5 mls). The etching with octane proceeded for 5 minutes, the octane was removed and the chamber refilled with oxygen. The procedure was repeated until the samples were judged to be hydrophobic by measurement of static water contact angle. Between each etching step the etcher was re-tuned where necessary.

The conditions used for the etching procedure were as shown in Table 1.

TABLE 1

Conditions of $O_2$/Octane Plasma Etching

| Stainless Steel | | |
|---|---|---|
| Atmosphere | $O_2$ | Ar/Octane |
| Forward Power | 90 W | 30 W |
| Reflected Power | 4 W | 3 W |
| Vacuum | 1 mBar | 3 mBar |
| Time | 3 × 5 min | 3 × 5 min |
| PTFE Tubing | | |
| Atmosphere | $O_2$ | Ar/Octane |
| Forward Power | 90 W | 65 W |
| Reflected Power | 4 W | 3 W |
| Vacuum | 2 mBar | 3 mBar |
| Time | 3 × 5 min | 3 × 5 min |
| Polypropylene | | |
| Atmosphere | $O_2$ | Ar/Octane |
| Forward Power | 90 W | 40 W |
| Reflected Power | 2 W | 2 W |
| Vacuum | 2½ mBar | 3 mBar |
| Time | 2 × 5 min | 2 × 5 min |
| Polyamide Mesh | | |
| Atmosphere | $O_2$ | Ar/Octane |
| Forward Power | 90 W | 25 W |
| Reflected Power | 2 W | 34 W |
| Vacuum | 2 mBar | 3 mBar |
| Time | 3 × 5 min | 2 × 5 min |

The etched, pre-treated samples were coated by dipping in a ppDAPC solution (10 mg/ml) in ethanol:chloroform (40:1), for 10 seconds. The samples were dried in air (30 seconds) and then dried throughly overnight in a laminar flow cabinet.

EXAMPLE 20

Plasma Etching and Silane Treatment

Samples of polyamide mesh, stainless steel needles. PTFE tubing and polypropylene were washed in hexane and dried. The samples were then placed in the etching chamber of a plasma barrel etcher (Bio-Rad RF Plasma Barrel Etcher PT7100). They were made hydrophilic by etching under an oxygen atmosphere at a chamber pressure of 1 mBar with a forward power of. 150 W and reflected power of 5 W. The etching was carried out for 2×5 minutes.

The samples were then silanated by treatment (for 16 hours) with octadecyl silane in chloroform (20%). Excess silane was removed by washing with chloroform (3 times). All samples were found to be hydrophobic as judged by static water content angle.

The etched, pre-treated samples were coated by dipping in a ppDAPC solution (10 mg/ml) in ethanol:chloroform (40:1), for 10 seconds. The samples were dried in air (30 seconds) and then dried throughly overnight in a laminar flow cabinet.

EXAMPLE 21

In vitro haemocompatibility testing of treated materials by platelet adhesion

A quantitative platelet adhesion test was carried out by immersing samples in fresh citrated whole human blood at room temperature for 30 minutes. Tubing samples were prepared in 3 cm lengths sealed at both ends (blood being introduced into the sample by hypodermic needle), and constantly mixed using a spiral mixer (tests were carried out in triplicate). Blood used in this assay was obtained using the double syringe method from three donors, 1, 2 and 3.

After incubation the samples were washed in isotonic phosphate buffered saline (PBS) and extracted in 1% trichloroacetate (TCA) (w/v) in 2 mM ethylene diamine tetraacetic acid (EDTA) to liberate ATP from any platelets adhering to the walls of the tubing.

The amount of ATP present in the extractant was estimated using the LKB Pharmacia ATP assay kit and a luminometer in accordance with the manufacturer's instructions.

The number of platelets adhering to the samples was estimated from a standard curve using ATP levels associated with a known number of platelets. The results for the PVC tubing prepared according to Example 1 are:

TABLE 2

| SAMPLE | DONOR | | | | % REDUCTION |
| --- | --- | --- | --- | --- | --- |
| | 1 | 2 | 3 | X̄ | |
| a) HARD PVC | | | | | |
| Uncoated Control | 4.45 | 7.57 | 4.05 | 5.36 | — |
| Coated 10 mg/ml ppDAPC | 0.03 | 0.04 | 0.02 | 0.03 | 99.4 |
| b) SOFT PVC | | | | | |

TABLE 2-continued

| SAMPLE | DONOR | | | | % REDUCTION |
| --- | --- | --- | --- | --- | --- |
| | 1 | 2 | 3 | X̄ | |
| Uncoated Control | 9.11 | 3.18 | 5.68 | 5.99 | — |
| Coated 10 mg/ml ppDAPC | 0.11 | 0.10 | 0.11 | 0.11 | 98 |

Substantial reductions in platelet adhesion to coated PVC are observed indicating that there is a large reduction in the thrombogenicity of PVC tubing after coating with ppDAPC.

The results for PE ribbon samples (2.2×3.3 cm$^2$) prepared according to Example 2 are:

TABLE 3

| SAMPLE | DONOR | | | | % REDUCTION |
| --- | --- | --- | --- | --- | --- |
| | 1 | 2 | 3 | X̄ | |
| Uncoated ribbon | 24.54 | 7.28 | 6.76 | 12.86 | — |
| PE ribbon coated with ppDAPC gamma-irradiated with 2.5 MRads m:p 90:10 | 1.31 | 2.83 | 0.96 | 1.70 | 87 |
| PE ribbon coated with ppDAPC gamma-irradiated with 5.0 MRads m:p = 88.12 | 1.42 | 1.38 | 0.40 | 1.07 | 92 |
| PE ribbon coated with ppDAPC gamma-irradiated with 7.5 MRads m:p = 76:24 | 1.08 | 2.02 | 0.82 | 1.31 | 90 |
| PE ribbon coated with pure polymer ppDAPC | 0.76 | 1.21 | 0.97 | 0.98 | 92 |

Results expressed as approximate number of platelets adhered × 10$^6$ per 7.26 cm$^2$ of material.
m:p = monomer:polymer ratio The results for catheters coated according to Example 4 are:

TABLE 4

| SAMPLE | DONOR | | | | % REDUCTION |
| --- | --- | --- | --- | --- | --- |
| | 1 | 2 | 3 | X̄ | |
| Uncoated PE catheter | 14.17 | 2.45 | 9.05 | 8.56 | — |
| PE coated with 10 mg/ml ppDAPC | 0.86 | 0.21 | 0.25 | 0.44 | 95 |

The results for PET woven filter material (4.84 cm$^2$) prepared according to Example 6 are:

TABLE 5

| SAMPLE | DONOR | | | | % REDUCTION |
| --- | --- | --- | --- | --- | --- |
| | 1 | 2 | 3 | X̄ | |
| 10 μm pore size | | | | | |
| Uncoated | 31.21 | 13.38 | 17.23 | 20.60 | — |
| Coated 2 mg/ml ppDAPC | 0.42 | 0.68 | 0.37 | 0.49 | 98 |
| Coated 5 mg/ml ppDAPC | 0.33 | 0.27 | 0.78 | 0.46 | 98 |
| 14 μm pore size | | | | | |

TABLE 5-continued

| SAMPLE | DONOR 1 | 2 | 3 | X̄ | % REDUCTION |
|---|---|---|---|---|---|
| Uncoated | 90.98 | 97.61 | — | 94.3 | — |
| Coated 20 mg/ml ppDAPC | 2.66 | 2.41 | — | 2.54 | 97 |

Results expressed as approximate number of platelets adhered × $10^6$ per 4.84 $cm^2$ samples of material.

Results for polypropylene hollow fibres prepared according to Example 10 are:

TABLE 6

| SAMPLE | DONOR 1 | 2 | 3 | X̄ | % REDUCTION |
|---|---|---|---|---|---|
| Uncoated | 4.08 | 4.07 | 16.95 | 8.36 | — |
| Coated 2 mg/ml ppDAPC | 0.09 | 0.31 | 0.24 | 0.21 | 97 |
| Coated 10 mg/ml ppDAPC | 0.23 | 0.20 | 0.13 | 0.19 | 98 |

Results expressed as approximate number of platelets × $10^6$ adhered per 20 cm length of hollow fibre.

The results for polystyrene petri dishes coated with ppDAPC according to Example 12 are:

TABLE 7

| SAMPLE | DONOR 1 | 2 | 3 | X̄ | % REDUCTION |
|---|---|---|---|---|---|
| Uncoated | 53.96 | 58.07 | 73.89 | 61.97 | — |
| Coated with 10 mg/ml ppDAPC | 6.55 | 4.51 | 15.48 | 8.85 | 86 |

The results from stainless steel rods coated according to Example 16 are:

TABLE 8

| SAMPLE | DONOR 1 | 2 | 3 | X̄ | % REDUCTION |
|---|---|---|---|---|---|
| Uncoated rod | 0.36 | 7.24 | 1.14 | 2.91 | — |
| Coated rod with 10 mg/ml ppDAPC | 0.04 | 0.13 | 0.04 | 0.07 | 98 |

Result expressed as approximate number of platelets adhered × $10^6$ per 3 cm length of material.

The results for polyimide prepared according to Example 17 are:

TABLE 9

| SAMPLE | DONOR 1 | 2 | 3 | X̄ | % REDUCTION |
|---|---|---|---|---|---|
| Uncoated Polyimide | 0.19 | 1.68 | 0.46 | 0.78 | — |
| Coated polyimide 10 mg/ml ppDAPC | 0.06 | 0.03 | 0.04 | 0.04 | 95 |

Results expressed as platelets adhered × $10^6$ per 10 cm length of material.

Results for IV catheters coated according to Example 18 are:

TABLE 10

| SAMPLE | DONOR 1 | 2 | 3 | X̄ | % REDUCTION |
|---|---|---|---|---|---|
| Uncoated | 4.10 | 9.36 | 11.98 | 8.48 | — |
| Coated with 10 mg/ml ppDAPC | 0.76 | 0.27 | 2.41 | 1.15 | 87 |

Results expressed as approximate number of platelets adhered × $10^6$ per 5 cm length of catheter Results for PTFE tubing, polyamide mesh and polypropylene material pre-treated with octane or octadecylsilane and then coated with ppDAPC according to Example 19 or 20 were as follows relative to material untreated by plasma etching or with ppDAPC.

TABLE 11

| SAMPLE | % REDUCTION IN PLATELET ADHESION |
|---|---|
| PTFE Tubing (Octane treatment-Ex 19) | 81 |
| PTFE Tubing (Silane treatment-Ex 20) | 69 |
| Polyamide Mesh (Octane treatment-Ex 19) | 88 |
| Polyamide Mesh (Silane treatment-Ex 20) | 92 |
| Polypropylene (Octane treatment-Ex 19) | 85 |
| Polypropylene (Silane treatment-Ex 20) | 49 |

EXAMPLE 22

In Vitro Clotting Times for Human Whole Blood

The clotting times in various uncoated and coated pharmaceutical vials were determined as follows:

1. 200 µl of fresh frozen plasma was prewarmed to 37° C. and added to the vial.
2. 200 µl of prewarmed (+37° C.) $CaCl_2$ (0.025M) was added to the vial and the timer started.
3. Vials were maintained at +37° C. by dipping into a +37° C. water bath.
4. Timer was stopped when the first clot was visible.

TABLE 12

| | | CLOTTING TIMES | |
|---|---|---|---|
| | SAMPLE | DONOR | TIME(S) |
| EXAMPLE 8 | Glass Uncoated | 1 | 81 |
| | | 2 | 205 |
| | Glass Coated with ppDAPC | 1 | 333 |
| EXAMPLE 5 | PET Uncoated | 1 | 361 |
| | | 2 | 593 |
| | PET Coated with ppDAPC | 1 | 413 |
| | | 2 | >480 |
| EXAMPLE 11 | Polypropylene Uncoated | 1 | 353 |
| | | 2 | 543 |
| | Polypropylene Coated with ppDAPC | 1 | 386 |
| | | 2 | 564 |
| EXAMPLE 9 | Glass Uncoated | 1 | 145 |
| | Silylated | 2 | 155 |
| | Glass Silylated and | 1 | 150[(1)] |

TABLE 12-continued

| CLOTTING TIMES | | |
|---|---|---|
| SAMPLE | DONOR | TIME(S) |
| coated with ppDAPC | 2 | 237 |

(1)Vial thought to have deficient coating.

In all tests the coated vials have a longer clotting time than uncoated indicating a less thrombogenic surface.

EXAMPLE 23

In Vitro Platelet Adhesion Observations by Scanning Electron Microscopy

Samples of material treated according to Example 13, 14, 15, 16 and 17 were incubated in fresh, titrated whole blood as described in Example 19 above. After removal from the blood these materials were washed using PBS and prepared for scanning electron microscopy by fixing in an aliquot of the following solution:

2 ml 25% glutaraldehyde
83 ml 0.15M PBS (pH 7.4)
15 ml saturated picric acid

The samples were washed in PBS and dehydrated using ethanol (70%), followed by absolute ethanol. Finally samples were sputter coated with gold (at 30 mA for 3 minutes) and observed under the electron microscope.

Electron microscopy shows that the ppDAPC-coated materials adhere fewer blood cells than untreated materials and that platelets are not activated by the treated materials. The ppDAPC-coated materials therefore appear less thrombogenic than the untreated materials.

Stainless steel, polyimide, silver, PVC, polyethylene, polypropylene and braided polyester were all judged less thrombogenic by this technique.

EXAMPLE 24

Fibrogen Deposition Studies

An enzyme linked immunosorbant assay is used which involves incubation of sample in human plasma then detection of adsorbed fibrinogen by a double antibody (the first antibody is specific for human fibrinogen and second antibody which is conjugated to horseradish peroxidase is specific for the first antibody).

Quantitation is achieved by determining HRPO activity on the surface.

Both the silanated and octane treated samples obtained as described in Examples 19 & 20 were tested coated and uncoated and the results expressed as reduction in protein adsorption on coated material as % of protein absorption on uncoated, as in Example 2.

Samples were included in the assay which consisted of ppDAPC coated polyethylene ribbon.

All samples were analysed in triplicate. The precision of the assay expressed as the average co-efficient of variation for the triplicate data points is about 10%.

TABLE 13

| SAMPLE | % REDUCTION IN FIBRINOGEN ADS. (RELATIVE TO UNCOATED) |
|---|---|
| S. Steel needle (silane treatment-Ex 20) | 64 |
| S. Steel needle (octane treatment-Ex 19) | 78 |
| PTFE Tubing (Silane treatment-Ex 20) | 72 |
| PFTE Tubing (Octane treatment-Ex 19) | 65 |
| Polyamide mesh (Silane treatment-Ex 20) | 68 |
| Polyamide mesh (Octane treatment-Ex 19) | 84 |
| Polypropylene rib (Silane treatment-Ex 20) | 83 |
| Polypropylene rib (Octane treatment-Ex 19) | 71 |
| Polypropylene end (Silane treatment-Ex 20) | 75 |
| Polypropylene end (Octane treatment-Ex 19) | 73 |
| Polyethylene (coated with ppDAPC Ex 2) | 78 |

EXAMPLE 25

Testing for Protein Adsorption by 2nd Derivative UV Spectroscopy

Procedure

One liter of borate buffer was prepared by dissolving sodium chloride (8.5 g), boric acid (4.6 g) and borax (0.4 g) in 1 liter of distilled water. The pH of this solution was then measured and was found to be 7.28. A lysozyme solution (1.2 mg/ml) was then prepared by dissolving 300 mg lysozyme in 250 ml berate buffer. The assay was started by addition of lysozyme solution (10 ml) to pharmaceutical vials which were either uncoated or coated with ppDAPC as described in Example 5, 8, 9 and 11. The samples were then incubated (37° C.) for 24 hours.

The absorbances of the samples were measured in the 2nd derivative mode and used to calculate the amount of protein adsorbed as shown below.

TABLE 14

Protein adsorption results on various coated materials

| | SAMPLE | AVERAGE mg Protein adsorbed | % REDUCTION |
|---|---|---|---|
| Control | Glass | 408.5 | — |
| Example 8 | Glass + 10 mg/ml ppDAPC | 113.4 | 72 |
| Example 9 | Glass + Silane + 10 mg/ml | 94.2 | 77 |
| Control | PET | 224.34 | — |
| Example 5 | PET + 10 mg/ml ppDAPC | 112.56 | 50 |
| Control | Polypropylene | 231.96 | — |
| Example 11 | Polypropylene + 10 mg/ml | 82.44 | 64 |

TABLE 14-continued

Protein adsorption results on various coated materials

| SAMPLE | AVERAGE mg Protein adsorbed | % REDUCTION |
|---|---|---|
| ppDAPC | | |

EXAMPLE 23

Determination of Total Amount of Coated Material and the Stability of the Coating A quantitative assay for ppDAPC was carried out by immersion of coated materials prepared in the earlier Examples in a colour reagent containing phospholipase D, choline oxidase, phenol and 4-aminoantipyrine. The samples were incubated (37° C.) for 20 minutes and the absorbance at 505 nm was measured using a Perkin-Elmer Lambda 15 uv/visible spectrometer. The concentration of coating material was determined by the use of a calibration curve of uncoated ppDAPC at known concentrations. Stability of coatings were assessed by incubation of the samples in PBS (37° C.) for 1 hour. The PBS was extracted with chloroform, the solvent removed and any lipid assayed by addition of colour reagent as above.

TABLE 15

Measurement of total coating and coating stability of PE ribbon coated according to Example 2
PE Ribbon

| SAMPLE | AVERAGE CONC. µg ppDAPC/cm$^2$ PE | AMOUNT OF COATING LEACHED AFTER 1 HOUR EXPOSURE TO PBS AT 37° C. |
|---|---|---|
| PE Control | — | — |
| 10 mg/ml ppDAPC 2.5 MRad gamma-irradiation | 23.5 | N.D |
| 10 mg/ml ppDAPC 5.0 MRad gamma-irradiation | 31.3 | N.D |
| 10 mg/ml ppDAPC 7.5 MRad gamma-irradiation | 23.0 | N.D |

N.D = Not Detected: below detectable limit for assay
Sample size = 25 mm × 25 mm

TABLE 16

Measurement of total coating and coating stability of catheters coated according to Example 4

| SAMPLE | CONC. µg ppDAPC/cm CATHETER | CONC. µg ppDAPC/cm CATHETER LEACHED AFTER 1 HOUR AT 37° C. (in PBS) | AVERAGE % LOSS |
|---|---|---|---|
| Control | — | — | — |
| 10 mg/ml ppDAPC Coated | 11.6–17.2 | 0.57–1.06 | 8% |

Sample length = 8 cm

TABLE 17

Measurement of total coating and coating stability of PET woven filter material coated according to Example 6

| SAMPLE | AVERAGE CONC. µg ppDAPC/cm$^2$ FLAT FILTER | AVERAGE CONC. LEACHED OF µg ppDAPC/cm$^2$ FLAT FILTER |
|---|---|---|
| 0.2 mg/ml ppDAPC | 0.103 | N.D |
| 2 mg/ml ppDAPC | 0.297 | N.D |
| 5 mg/ml ppDAPC | 0.530 | N.D |

N.D = Not detectable i.e. below detectable limits of assay
Sample size = 35 mm × 35 mm squares

TABLE 18

Measurement of total coating and coating stability on polypropylene hollow fibres according to Example 10

| SAMPLE | AVERAGE CONC. µg ppDAPC/cm PP | AMOUNT OF COATING LEACHED AFTER 1 HOUR EXPOSURE TO PBS AT 37° C. |
|---|---|---|
| Control | — | — |
| 2 mg/ml ppDAPC Coated PP | 1.25 | N.D |
| 10 mg/ml ppDAPC Coated PP | 3.3 | N.D |

Sample length = 15 cm
N.D. Not detected i.e. below detectable limit of assay

TABLE 19

Measurement of total coating and coating stability of PE ribbon coated with mixed lipids according to Example 3

| SAMPLE ppDAPC:DMPC Mixture of PE | AVERAGE CONC. µg P/cm$^2$ | AVERAGE AMOUNT OF LEACHED COATING AFTER 1 HOUR EXPOSURE TO PBS AT 37° C. µg P/cm$^2$ |
|---|---|---|
| Control | — | — |
| 25%:75% | 0.73 | N.D |
| 50%:50% | 0.67 | N.D |
| 75%:25% | 0.67 | N.D |
| ppDAPC:DPPC Mixture on PE | | |
| 25%:75% | 0.72 | N.D |
| 50%:50% | 0.66 | N.D |
| 75%:25% | 0.85 | N.D |

N.D = Not detected i.e. beyond detectable limits of assay

TABLE 20

| | CONTACT ANGLE | |
|---|---|---|
| SAMPLE | BEFORE COATING | AFTER COATING WITH 10 mg/ml ppDAPC |
| Polyethylene Ribbon (coated as in Example 2) | 82, 83, 81, 79 | 12, 11, <5, 12 |
| PVC Tubing (Soft) (coated as in Example 1) | 79, 71, 74, 77 | 38, 24, 30, 40 |
| PVC Tubing (Hard) (coated as in Example 1) | 81, 77, 84, 74 | <5, <5, 25, 21 |

EXAMPLE 27

Testing of the Spreading of Water on Treated Surfaces

PE ribbon coated with ppDAPC using the procedure of Example 2 was tested for wettability using the Wilhelmy slide technique. The dynamic contact angle decreased from 89° before coating to 56° after coating.

The static contact angle was measured for various substrates coated with ppDAPC by the addition of a 5 µl water droplet and measuring angle of contact of the substrate with a horizontal microscope.

In all cases, after coating with ppDAPC a marked decrease occurred in the angle of contact indicating a surface is produced with increased wettability.

EXAMPLE 28

Protein Adsorption on PVC Tubing Coated with ppDAPC Determined by SDS Gel Electrophoresis Untreated and coated PVC tubing treated as in Example 1 were placed into 5 ml plastic tubes with 2 mls of Fresh Frozen Plasma (FFP). Tubes were rotated on a spiral mixer for one hour at room temperature.

The plasma was decanted and each sample rinsed several times with 0.02M Tris/0.16M NaCl pH 7.5. Each sample was left to wash with buffered saline for 5 minutes at room temperature. The samples were rinsed several times as before and washed for a further 5 minutes. The washing was repeated one more.

Samples were placed in new, dry tubes and 300 μl of SDS PAGE sample buffer was added. The tubes were left to rotate at room temperature overnight.

A 20 μl sample of buffer was removed from each tube, boiled for 2 minutes and run on SDS PAGE under reducing conditions. The gels were stained using Coomassie Blue Pa50 stain and examined for protein bands.

A notable reduction in the range and amount of proteins adsorbed was detected indicating the surface is rendered more biocompatible by coating with ppDAPC.

EXAMPLE 29

Lubricity of ppDAPC Coatings

Catheters coated according to Example 4 were tested for coating lubricity using an Instron device. The force required to pull the coated catheters through a die at 2"/min was reduced to half following coating with ppDAPC.

EXAMPLE 30

Reduction of Surface Charge

A coating of ppDAPC onto quartz cuvettes pre-treated with monochlorooctadecyl silane to produce a hydrophobic surface significantly reduced the net surface charge. The wall potential was reduced to a few mV. ppDAPC coating may therefore be used in the electronics industry and in electrochemical detection/analysis where electrostatic charge or interfering background charge needs to be minimised.

We claim:

1. A process for coating a surface comprising applying to the surface a solution of a polymer, in an organic solvent and removing the solvent, wherein the polymer is obtained by polymerizing a phospholipid of formula (I):

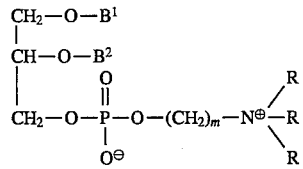

wherein at least one of $B^1$ and $B^2$ is a group of the formula (II):

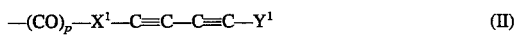

wherein p is 0 or 1, $X^1$ is an aliphatic or cycloaliphatic group, $Y^1$ is H or a monovalent aliphatic or cycloaliphatic group, the total number of carbon atoms in $X^1$ and $Y^1$ in each $B^1$ and/or $B^2$ being 8 to 26, and the other of $B^1$ and $B^2$ is either (a) the same or a different group of the formula (II) or (b) is an aliphatic or cycloaliphatic group containing at least 8 carbon atoms; m is 2, 3 or 4 and each R independently represents an alkyl group containing 1 to 4 carbon atoms;

wherein said polymer contains repeating units of the following formula (III)

wherein one of $Z^1$ and $Z^2$ is $Y^1$ as defined above, and one of $Z^3$ and $Z^4$ are $Y^1$ as defined above, and wherein the other one of $Z^1$ and $Z^2$ and the other one of $Z^3$ and $Z^4$ are the formula $-X^1-(CO)_p-G$, wherein $X^1$ and p are as defined above, and G is a corresponding remaining portion of the phospholipid of formula (I).

2. A process according to claim 1 in which the surface is a blood-contacting surface.

3. A process according to claim 1 in which the surface is subject to non-specific adsorption of protein.

4. A process according to claim 1, wherein in the phospholipid of formula (I), $B^1$ and $B^2$ are identical or different groups of the formula (II).

5. A process according to claim 1 wherein in the phospholipid of formula (I), each group $B^1$ and/or $B^2$ of formula (II) contains from 20 to 26 carbon atoms excluding any carbonyl carbon atoms.

6. A process according to claim 1 wherein in the phospholipid of formula (I), the number of carbon atoms in each $X^1$ is such that the di-yne will undergo both intramolecular and intermolecular polymerisation on exposure to actinic radiation.

7. A process according to claim 1 wherein in the phospholipid of formula (I) $B^1$ and $B^2$ each represent

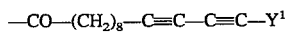

wherein the groups $Y^1$ are the same or different.

8. A process according to claim 1 wherein in the phospholipid of formula (I) m is 2 and each R is methyl.

9. A process according to claim 1 wherein the phospholipid of formula (I) is:

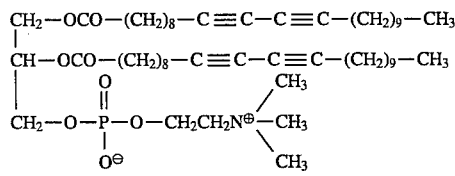

10. A process according to claim 1 wherein the phospholipid of formula (I) is:

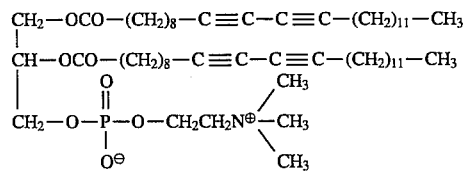

11. A process according to claim 1 wherein said solution also contains said phospholipid of said formula (I).

12. A process according to claim 1 wherein a mixture comprising a polymer obtained from a phospholipid of formula (I) and a diester of phosphatidyl choline is applied to the surface.

13. A process according to claim 12 wherein the diester of phosphatidyl choline is dipalmitoyl phosphatidyl choline, dimyristoyl phosphatidyl choline or distearoyl phosphatidyl choline.

14. A process according to claim 1 which comprises treating the surface to increase the hydrophobicity of the surface, prior to coating with the polymer.

15. A process according to claim 14 wherein said treating the surface is effected by a reactive alkyl silane or plasma polymerized in the presence of an alkane or alkyl silane.

16. A process according to claim 1 wherein the surface is coated with said solution of said polymer in a lower alkanol or halogenated alkane or a mixture thereof.

17. A process according to claim 1 wherein said solution comprises from 0.5 to 35 mg/ml of said polymer.

18. A process according to claim 1 wherein said solution is coated upon said surface by immersion in a coating bath, spraying, or spin coating.

19. A process according to claim 1 wherein the coating has a thickness of from 3 to 1000 nm.

20. A process for coating a surface comprising the steps of
   (a) treating said surface with a reactive alkyl silane or plasma polymerizing said surface in the presence of an alkane or alkylsilane,
   (b) after step (a) coating said surface with a solution of a polymer in a solvent selected from the group comprising lower alkanols, halogenated alkanes and mixtures thereof containing from 0.5 to 35 mg/ml of said polymer, by immersion in a coating bath, spraying, or spin coating and
   (c) removing said solvent,
wherein said polymer is a phospholipid of formula (I)

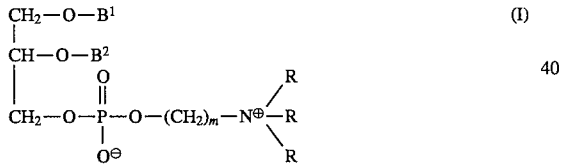

wherein at least one of $B^1$ and $B^2$ is a group of the formula (II):

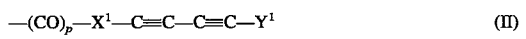

wherein p is 0 or 1, $X^1$ is an aliphatic or cycloaliphatic group, $Y^1$ is H or a monovalent aliphatic or cycloaliphatic group, the total number of carbon atoms in $X^1$ and $Y^1$ in each $B^1$ and/or $B^2$ being 8 to 26, and the other $B^1$ and $B^2$ is either (a) the same or a different group of the formula (II) or (b) is an aliphatic or cycloaliphatic group containing at least 8 carbon atoms; m is 2, 3 or 4 and each R independently represents an alkyl group containing 1 to 4 carbon atoms.

21. The process according to claim 1 wherein said process forms a coating having a thickness of 10–500 nm by applying said solution.

22. A process for coating a surface comprising applying to said surface a solution of a polymer, in an organic solvent and then removing the solvent, wherein the polymer is obtained by polymerizing a phospholipid of formula (I):

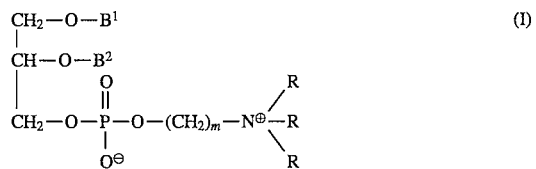

wherein at least one of $B^1$ and $B^2$ is a group of the formula (II):

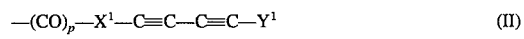

wherein p is 0 or 1, $X^1$ is an aliphatic or cycloaliphatic group, $Y^1$ is H or a monovalent aliphatic or cycloaliphatic group, the total number of carbon atoms in $X^1$ and $Y^1$ in each $B^1$ and/or $B^2$ being 8 to 26, and the other of $B^1$ and $B^2$ is either (a) the same or a different group of the formula (II) or (b) is an aliphatic or cycloaliphatic group containing at least 8 carbon atoms; m is 2, 3 or 4 and each R independently represents an alkyl group containing 1 to 4 carbon atoms;

wherein said polymer contains repeating units of the following formula (III):

wherein one of $Z^1$ and $Z^2$ is $Y^1$, and one of $Z^3$ and $Z^4$ are $Y^1$, wherein the other one of $Z^1$ and $Z^2$ and the other one of $Z^3$ and $Z^4$ are the formula —$X^1$—$(CO)_p$—G, wherein $X^1$ and p are as defined above, and G is a corresponding remaining portion of the phospholipid of formula (I), wherein said solution comprises from 0.5 to 35 mg/ml of said polymer, wherein said process forms a coating having a thickness of from 3 to 1000 nm by application of said solution, wherein in said phospholipid of formula (I), $B^1$ and $B^2$ each represent

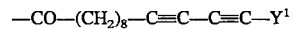

wherein the groups $Y^1$ are the same or different.

23. The process according to claim 22 wherein said process forms a coating having a thickness of 10 to 500 nm by applying said solution.

24. A process for coating a surface comprising:
   pre-treating said surface by plasma polymerization,
   covering said surface with a coating comprising a polymer in a solution in an organic solvent, wherein said polymer is obtained by polymerizing a phospholipid of formula (I):

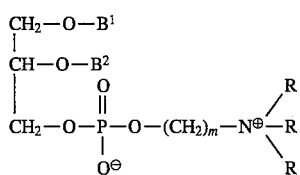 (I)

wherein at least one of $B^1$ and $B^2$ is a group of the formula (II):

$$-(CO)_p-X^1-C{\equiv}C-C{\equiv}C-Y^1 \quad (II)$$

wherein p is 0 or 1, $X^1$ is an aliphatic or cycloaliphatic group, $Y^1$ is H or a monovalent aliphatic or cycloaliphatic group, the total number of carbon atoms in $X^1$ and $Y^1$ in each $B^1$ and/or $B^2$ being 8 to 26, and the other of $B^1$ and $B^2$ is either (a) the same or a different group of the formula (II) or (b) is an aliphatic or cycloaliphatic group containing at least 8 carbon atoms; m is 2, 3 or 4 and each R independently represents an alkyl group containing 1 to 4 carbon atoms;

wherein said polymer contains repeating units of the following formula (III):

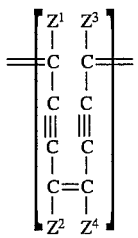 (III)

wherein one of $Z^1$ and $Z^2$ are $Y^1$ as defined above, and one of $Z^3$ and $Z^4$ are $Y^1$ as defined above, and wherein the other one of $Z^1$ and $Z^2$ and the other one of $Z^3$ and $Z^4$ are the formula $-X^1-(CO)_p-G$, wherein $X^1$ and p are as defined above, and G is a corresponding remaining portion of the phospholipid of formula (I), and then removing said organic solvent.

\* \* \* \* \*